US005767106A

United States Patent [19]

Turley et al.

[11] Patent Number: 5,767,106
[45] Date of Patent: Jun. 16, 1998

[54] TREATMENT OF DISEASE AND CONDITIONS ASSOCIATED WITH MACROPHAGE INFILTRATION

[75] Inventors: Eva Anne Turley, Winnipeg; Samuel Simon Asculai, Toronto, both of Canada

[73] Assignee: Hyal Pharmaceutical Corporation, Mississauga, Canada

[21] Appl. No.: 295,390

[22] Filed: Aug. 25, 1994

Related U.S. Application Data

[63] Continuation-in-part of Ser. No. 675,908, Jul. 3, 1991, and a continuation-in-part of Ser. No. 200,309, Feb. 23, 1994, Pat. No. 5,674,857, which is a continuation of Ser. No. 838,673, Feb. 21, 1992, abandoned.

[30] Foreign Application Priority Data

Aug. 24, 1994 [CA] Canada .................................. 2130762

[51] Int. Cl.$^6$ ......................................................... A61K 31/70
[52] U.S. Cl. .................................................................. 514/54
[58] Field of Search .............................. 536/55.1, 55.3; 514/54

[56] References Cited

U.S. PATENT DOCUMENTS

| 2,583,096 | 1/1952 | Hadidian et al. . |
| 3,042,667 | 7/1962 | Flodin et al. . |

(List continued on next page.)

FOREIGN PATENT DOCUMENTS

| B-72117/87 | 12/1987 | Australia . |
| B-15456/88 | 10/1988 | Australia . |
| B-14534/88 | 11/1988 | Australia . |
| 1087610 | 10/1980 | Canada . |
| 1205031 | 5/1986 | Canada . |
| 1240929 | 8/1988 | Canada . |
| 2006060 | 12/1989 | Canada . |
| 2004740 | 6/1990 | Canada . |
| 2031880 | 12/1990 | Canada . |
| 1317287 | 5/1993 | Canada . |
| 0138216 | 4/1985 | European Pat. Off. . |
| 0138572 | 4/1985 | European Pat. Off. . |
| 0136782 | 10/1985 | European Pat. Off. . |
| 0197718 | 10/1986 | European Pat. Off. . |
| 0224987 | 6/1987 | European Pat. Off. . |
| 0244178 | 11/1987 | European Pat. Off. . |
| 0296740 | 12/1988 | European Pat. Off. . |
| 0341745 | 11/1989 | European Pat. Off. . |
| 0378852 | 7/1990 | European Pat. Off. . |
| 0433817 | 6/1991 | European Pat. Off. . |
| 0437622-A1 | 7/1991 | European Pat. Off. . |
| 1425265 | 4/1966 | France . |
| 2364373 | 7/1975 | Germany . |
| 57-185208 | 11/1982 | Japan . |
| 58-183611 | 10/1983 | Japan . |
| 58-183938 | 10/1983 | Japan . |
| 59-025311 | 2/1984 | Japan . |
| 59-219209 | 12/1984 | Japan . |
| 61-056114 | 3/1986 | Japan . |
| 61-064701 | 4/1986 | Japan . |
| 61-106602 | 5/1986 | Japan . |
| 61-171703 | 8/1986 | Japan . |
| 61-187866 | 8/1986 | Japan . |
| A-62-201825 | 9/1988 | Japan . |
| 1238530 | 9/1989 | Japan . |
| A-116678/88 | 11/1989 | Japan . |
| 27287 | 1/1990 | Japan . |
| 2200624 | 8/1990 | Japan . |
| 4-18022 | 1/1992 | Japan . |
| 769287 | 5/1955 | United Kingdom . |
| 818336 | 8/1959 | United Kingdom . |
| 1283892 | 8/1972 | United Kingdom . |
| 2099826 | 12/1982 | United Kingdom . |
| WO 84/04453 | 11/1984 | WIPO . |
| WO 86/00912 | 2/1986 | WIPO . |
| WO 86/03125 | 6/1986 | WIPO . |
| WO 88/06840 | 9/1988 | WIPO . |
| WO 88/07060 | 9/1988 | WIPO . |
| WO 88/07853 | 10/1988 | WIPO . |
| WO 89/03205 | 4/1989 | WIPO . |
| WO 89/05645 | 6/1989 | WIPO . |
| WO 89/10941 | 11/1989 | WIPO . |
| WO 90/10020 | 9/1990 | WIPO . |
| WO 90/10031 | 9/1990 | WIPO . |

OTHER PUBLICATIONS

Abatangelo G. Martelli M. Vecchia P. Healing of hyaluronic acid–enriched wounds: Histological observations. *J. Surgical Research* 1983; 35: 410–416.

Abatangelo G. Corvito R. et al. Cell detachment mediated by hyaluronic acid. *Exp. Cell Res.* 1982; 137: 73–78.

Adams JB Steroid hormones and breast cancer. *Dissertation Abstracts International* 1981; 42(4): 1425B.

Ahlgren T. Jarstrand C. Hyaluronic acid enhances phagocytosis of human monocytes in vitro. *J Clinical Immunology* 1984; 4(3): 246–249.

Alaverdyan ML. Ter–Avetisyan AT. Effect of hyaluronidase, hyaluronic acid, and some other substances on postradiational experimental bacteriemai. *Bulletin of Experimental Biology and Medicine* 1967; 64(9): 967–969.

Alexander P. Ageing skin: Remedial measures. *Manuf. Chemist* 1985; Oct.: 35, 37, 39.

Altman RD. Kapila P. Dean DD. Howell DS. Future therapeutic trends in osteoarthritis. *Scand. J. Rheumatology* 1989; Suppl. 77: 37–42.

Ambroggio G. Barberis ML Trattamento di lesioni cutanee ad andamento cronico con acido ialuronico. *Minerva Chirurgica* 1969; 23(15): 815–818.

(List continued on next page.)

*Primary Examiner*—Elli Peselev
*Attorney, Agent, or Firm*—Ivor M. Hughes; Neil H. Hughes; Marcelo K. Sarkis

[57] ABSTRACT

A method of treating a human having a disease or condition characterized by macrophage, neutrophile or other white blood cell infiltration into the area damaged by the disease or condition, the method comprising administering to the human an effective amount of hyaluronic acid and/or salts thereof for a period of time until the administration is no longer required.

10 Claims, No Drawings

U.S. PATENT DOCUMENTS

| | | |
|---|---|---|
| 3,357,784 | 12/1967 | Kasper et al. |
| 3,396,081 | 8/1968 | Billek et al. |
| 3,436,454 | 4/1969 | Nouvel . |
| 3,792,164 | 2/1974 | Bechtold et al. |
| 3,845,201 | 10/1974 | Haddad et al. |
| 3,870,791 | 3/1975 | Haddad et al. |
| 3,887,703 | 6/1975 | Manoussos et al. |
| 4,003,991 | 1/1977 | Krohn et al. |
| 4,045,558 | 8/1977 | Smith et al. |
| 4,061,722 | 12/1977 | Bodor et al. |
| 4,141,973 | 2/1979 | Balazs . |
| 4,240,163 | 12/1980 | Galin . |
| 4,255,415 | 3/1981 | Chrai et al. |
| 4,271,143 | 6/1981 | Schoenwald et al. |
| 4,272,522 | 6/1981 | Balazs . |
| 4,280,954 | 7/1981 | Yannas et al. |
| 4,303,676 | 12/1981 | Balazs . |
| 4,328,803 | 5/1982 | Pape . |
| 4,470,975 | 9/1984 | Berger et al. |
| 4,478,822 | 10/1984 | Haslam et al. |
| 4,487,865 | 12/1984 | Balazs et al. |
| 4,500,676 | 2/1985 | Balazs . |
| 4,517,295 | 5/1985 | Bracke . |
| 4,582,865 | 4/1986 | Balazs et al. |
| 4,629,623 | 12/1986 | Balazs et al. |
| 4,636,524 | 1/1987 | Balazs et al. |
| 4,684,627 | 8/1987 | LeVeen et al. |
| 4,686,288 | 8/1987 | Lormeau et al. |
| 4,711,780 | 12/1987 | Fahim . |
| 4,713,448 | 12/1987 | Balazs et al. |
| 4,716,224 | 12/1987 | Sakurai et al. |
| 4,725,585 | 2/1988 | Wenge et al. |
| 4,736,024 | 4/1988 | Della Valle et al. |
| 4,746,504 | 5/1988 | Nimrod et al. |
| 4,755,544 | 7/1988 | Makino et al. |
| 4,782,046 | 11/1988 | Brown et al. |
| 4,784,990 | 11/1988 | Nimrod et al. |
| 4,784,991 | 11/1988 | Nimrod et al. |
| 4,795,741 | 1/1989 | Leshchiner et al. |
| 4,801,619 | 1/1989 | Lindblad . |
| 4,804,537 | 2/1989 | Bergman et al. |
| 4,808,576 | 2/1989 | Schultz et al. |
| 4,814,175 | 3/1989 | Tack et al. |
| 4,820,732 | 4/1989 | Shell et al. |
| 4,840,941 | 6/1989 | Ueno et al. |
| 4,851,521 | 7/1989 | della Valle et al. |
| 4,853,224 | 8/1989 | Wong . |
| 4,853,226 | 8/1989 | Machida et al. |
| 4,855,134 | 8/1989 | Yamahira et al. |
| 4,863,907 | 9/1989 | Sakurai et al. |
| 4,877,619 | 10/1989 | Richer . |
| 4,879,282 | 11/1989 | Saliba, Jr. |
| 4,912,093 | 3/1990 | Michaeli . |
| 4,913,898 | 4/1990 | Altobelli et al. |
| 4,937,254 | 6/1990 | Sheffield et al. |
| 4,937,270 | 6/1990 | Hamilton et al. |
| 4,944,941 | 7/1990 | Ammann . |
| 4,957,744 | 9/1990 | della Valle . |
| 4,963,666 | 10/1990 | Malson . |
| 4,965,353 | 10/1990 | della Valle . |
| 5,092,841 | 3/1992 | Spears . |
| 5,095,037 | 3/1992 | Iwamitsu . |
| 5,116,331 | 5/1992 | della Valle . |
| 5,116,864 | 5/1992 | March et al. |
| 5,202,431 | 4/1993 | della Valle et al. ............... 536/55.1 |

OTHER PUBLICATIONS

Anastassiades T, Robertson W Modulation of mitogen–dependent lymphocyte stimulation by hyaluroniccid. *J Rheum.* 1984; 11(6): 729–734.

Appel A, Horwitz AL, Dorfman A. Cell–free synthesis of hyaluronic acid in marfan syndrome. *J Biological Chemistry* 1979; 254(23): 12199–12203.

Arzeno G. Miller D. Effect of sodium hyaluronate on corneal wound healing. *Arch Ophthalmol* 1982; 100: 152.

Aste L. Burattoni G. Osservazioni sull'impiego dell'acido jaluronico nel trattamento delle ulcere da decubito nelle sindromi midollari. *Ospedali D'Italia Chirurgia* 1967: 17(3): 315–322.

Balazs EA, Band P. Hyaluronic acid: Its structure and use. *Cosmetics & Toiletries*. Polymers in Cosmetics 1984; 99: 65–72.

Balazs EA, Freeman MI, et al. Hyaluronic acid and replacement of vitreous and aqueous humor. *Modern Problems in Ophthalmology: Secondary Detachment of the Retina* 1971; 10: 3–21.

Balazs EA, Gibbs DA. The rheological properties and biological function of hyaluronic acid. In: *Chemistry and Molecular Biology of the Intercellullar Matrix. Vols. III.* New York: Academic Press, 1970. pp. 1241–1253.

Barondes SH. Bifunctional properties of lectins: Lectins redefined. *TIBS* 1988; 13 (Dec.): 480–482.

Barron BA, et al. Comparison of the effects of viscoat and healon on postoperative intraocular pressure. *Am. J. Ophthallmology* 1985; 100: 377–384.

Bayer EA, Wilcher M. The use of the avidin–biotin complex as a tool in molecular biology. *Methods of Biochemical Analysis.* Vol. 26: 1–45.

Ber A, Mikolajczyk H. Badania nad ukladem hialuronidaza—kwas hialuronowy. Wplyw kwasu hialuronowego na gojenie sie doswiad–czalnych wrzodow zoladka u szczurow. *Patologia Polska* 1957; 8: 31–36.

Biggar WD, Sturgess JM. Role of lysozyme in the microbicidal activity of rat alveolar macrophages. *Infection and Immunity* 1977; 16(3): 974–982.

Billek G, Billek D. Hyaluronsaure –Die Gesch . . . eines kosmetischen wirkstoffs. [Summary in English] *Parfuemerie und Kosmetik* 1988; 69(12): 768–790 & 792–795.

Binkhorst CD. Advantages and disadvantages of intracamerular Na–Hyaluronate (Healon) in intraocular lens surgery. *Documenta Ophthalmologica* 1981; 50: 233–235.

Blumenkrantz N, Asboe–Hansen G. Reaction of cationic groups of chlorpromazine with anionic macromolecules: Complexes with DNA, RNA, hyaluronic acid and heparin. *Acta Pharmacol. et Toxiicol.* 1974; 34: 27–32.

Boutet D, Voskamp K. L'acide hyaluronique: Proprietes et applications. *Parfums, Cosmetiques, Aromes* 1986; 68: 53–56.

Bowen BR, Nguyen T, Lasky LA. Characterization of a human homologue of the murine peripheral lymph node homing receptor. *J Cell Biology* 1989; 109(Jul.): 421–427.

Boyce ST, Christianson DJ, Hansbrough JF. Structure of a collagen–GAG dermal skin substitute optimized for cultured human epidermal keratinocytes. *J. Biomedical Material Research* 1988; 22: 939–957.

Brandstetter W, Kiesewetter E, Wohlzogen FX. Influencing experimental pathological changes i rodents with hyaluronic acid. [Translation of: Beeinflussung experimentell–pathologischer veranderungen bei nagern durch hyaluronsaure.] *Archive for Experimental Pathology and Pharmacology/ Archiv Fur Experimentelle Pathologie* 1957; 231(2): 186–198.

Brandt K. Modification of chemotaxis by synovial fluid hyaluronate. *Arthritis and Rheumatism* 1970; 13(3): 308–309.

Brown TA, Bouchard T, St. John T, Wayner E, Carter WG. Human keratinocytes express a new CD44 core protein (CD44E) as a heparan–sulfate intrinsic membane proteoglycan with additional exons. *J Cell Biology* 1991; 113(1): 207–221.

Bruno RN. Osservazioni sull'impiego comparativo di sale sodico dell'acido ialuronico e dell'estratto di *Triticum vulgaris* in 20 casi di soggetti affetti da ulcere a deversa etiologia. [Summary in English] *Il Policlinico. Sezione Medica:* 1983; 90(4): 340–344.

Burk DT. Morphological effects of streptomyces hyaluronidase treatment on the ouitgrowth of the nasal processes in mouse embryos. *J Craniofacial Genetics* 1985; 5: 385–398.

Buu–Hoi NG, PH. La B–hydroxypropiophenone, ses analogues et leurs derives. *Recueil Trav. Chim. Pays–Bas* 1949; 68: 759, 768, & 774.

Camber O, Edman P, Gurny R. Influence of sodium hyaluronate on the meiotic effect of pilocarpine in rabbits. *Current Eye Research* 1987; 6(6): 779–784.

Camber O, Lundgren P. Diffusion of some low molecular weight compounds in sodium hyaluronate. *Acta Pharmaceutica Suecica* 1985; 22(6): 315–320.

Carbonetto S, Gruver MM, Turner DC. Nerve Fiber growth in culture on fibronectin, collagen, and glycosaminoglycan substrates. *J. Neuroscience* 1983; 3(11): 2324–2335.

Chang N–S. Hyaluronic acid and complement interactions. *Dissertation Abstracts International* 1985; 45(12): 3766–B.

Chang S–C. Pro–drug and vehicle approaches to improve the therapeutic index of topically applied timolol in the pigmented rabbit. *Dissertation Abstracts International* 1988; 49(2): 367–B.

Chen WYJ, Grant ME, Schor AM, Schor SL. Differences between adult and foetal fibroblasts in the regulation of hy: Correlation with migratory activity. *J Cell Science* 1989; 94: 577–584.

Cifonelli JA. The isolation and characterization of hyaluronic acid from *Pasteurella multocida. Carbohydrate Research* 1970; 14: 272–276.

Cifonelli JA, Dorfman A. The biosynthesis of hyaluronic acid by group A Streptococcus: The uridine nucleotides of groups A Streptococcus. *J. Biological Chemistry* 1957; 228: 547–557.

Cleary PP, Larkin A. Hyaluronic acid capsule: Strategy for oxygen resistance in group A streptococci. *J Bacteriology* 1979; 140(3): 1090–1097.

Cleland RL. Molecular weight distribution in hyaluronic acid. In: *Chemistry and Molecular Biology of the Intercellular Matrix.* Edited by E A Balazs. Boston: Academic Press, 1970: 733–742.

Comper WD, Laurent TC. Physiological function of connective tissue polysaccharides. *Physiological Reviews* 1978 (Jan.); 58(1): 255–305.

Constable IJ, Swann DA. Vitreous substitution. Chapter 60; pp. 709–713.

Constantini A, Muzzio A, Agus GB. Plethysmographic patterns in scleroderma after percutaneous G.A.G. treatment. *Bolletinno Chimico Farmaceutico* 1986; 125(10): 111s–115s.

Cravioto RO, Massieu GH, Izquierdo JJ. Effects of precipitates formed by insulin with hyaluronic acid and mucoid from vitreous humor in depressing blood–sugar levels. *Science* 1950; 111: 520–521.

Cullis–Hill D, Ghosh P. The role of hyaluronic acid in joint stability: A hypothesis for hip dysplasisa and allied disorders. *Medical Hypothesis* 1987; 23: 171–185.

Culty M, Miyake K, Kincade PW, Silorski E, Butcher EC. The hyaluronate receptor is a member of the CD44 (H–CAM) family of cell surface glycoproteins. *J Cell Biology* 1990; 111(6, pt. 1): 2765–2774.

Curri SB. Influence of the hyaluronic acid on the restoration processes of the muscular–cutaneous planes. [Translation of: Influenza dell'acido jaluronico sui processi riparativi dei piani cutaneo–muscolari.] *Bulletin of the Italian Society for Experimental biology/Bollettino Della Societa Italiana Di Biologia Sperimentale* 1959; 35(23): 1762–1768.

Dahl IM. Biosynthesis of proteoglycans and hyaluronate in human fibroblast cultures established from normal and pathological corneas. *Exp. Eye Research* 1981; 32: 435–443.

Dahlgren C, Bjorksten B. Effect of hyaluronic acid on polymorphonuclear leucocyte cell surface properties. *Scand. J Haematol.* 1982; 28: 376–380.

Dasch W, von, Braun E, Nowack H. Transdermale salicylat–resorption und verhalten des corticosteroid–plasmaspiegels nach epidermaler applikation einer antiphlogistisch wirksamen salbe. [Summary in English] *Arzneim.–Forsch.* 1983; 33(8): 1196–1199.

Davidson JF, Walker ID. Synthetic fibrinolytic agents. *Progress in Cardiovascular Diseases* 1979; XXI(5): 375–396.

De Buman M, Walther M, de Weck R. Wirksamkeit der Alphastria–Creme bei der Vorbeugung von Schwangerschaftsstreifen (Striae distensae). [Summary in English] *Gynak. Rdsch.* 1987; 27: 79–84.

Deguchi T, Ishii A, Tanaka M. Binding of aminoglycoside antibiotics to acidic mucopolysaccharides. *The Journal of Antibiotics* 1978; 31(2): 150–155.

Delmage JM, Powars DR, Jaynes PK, Allerton SE. The selective suppression of immunogenicity by hyaluronic acid. *Annals of Clinical and Laboratory Science* 1986; 16(1): 303–310.

Delpech A, Delpech B, Girard N, Boullie MC, Lauret P. Hyaluronectin in normal human skin and in basal cell carcinoma. *British J Dermatology* 1982; 106: 561–568.

Di Cicco LM, Mansbridge JN, Morhenn VB. Inhibition of attachment and growth of tumor cells on collagen by a monoclonal antibody. *In Vitro Cellular & Developmental Biology* 1987; 23(12): 805–814.

Dionigi R, Tibaldeschi C, et al. Comportamento dei mucopolisaccaridi acidi nel tessuto di riparazione delle ferite durante il processo di guarigione. *Biochimica E Biologia Sperimentale* 1968; 7(3): 153–156.

Doege KJ, Sasaki M, Kimura T, Yamada Y. Complete coding sequence and deduced primary structure of the human cartilage large aggregating proteoglycan, Aggrecan. *J Biological Chemistry* 1991; 266(2): 894–902.

Doillon CJ, Silver FH. Collagen–based wound dressing: Effects of hyaluronic acid and fibronectin on wound healing. *Biomaterials* 1986; 7(Jan.): 3–8.

Drobnik J. Hyaluronan in drug delivery. *Advanced Drug Delivery Reviews* 1991; 7: 295–308.

Dziewonski K, Kahl W. Studja nad reakcjami t. zw. merkuryzacji i degradacji kwasow wielokarbonowych. – Studien uber die Mercurie–rungs und Decarboxylierngstreaktionen von Polycarbonsauren. *Bull. Acad. Pol. Sci. Ser. Sci. Chim.* 1934: pp. 394–397.

Eisner G. Die Anwendung von Healon bei extrakapsularer kataraktextraktion und bei der implantation von intraokularen linsen. *Klin. Mbl. Augenheilk* 1981; 179: 346–349.

Elling H. Immunofluorescence demonstration of transdermal deposition of mucopolysaccharides into the skin. *Arzneim.-Forsch.* 1987; 37(7): 816–818.

Elling H. Penetration of mucopolysaccharides into the skin of diverse animal species. *Arzneim–Frosch.* 1986; 36(10): 1505–1507.

Elling H. Transcutaneous penetration of a mucopolysaccharide polysulfuric acid ester in man: A histochemical study. *Arzneim–Forsch.* Drug Res. 1987; 31(2): 212–213.

Faber V, Rosendal K. *Streptococcal hyaluronidase* II: Studies on the production of hyaluronidase and HA by representatives of all types of hemolytic streptococci belonging to group A. In: *Statens Seruminstitut, Copenhagen (Director: J. Orskov, M. D.).*

Fatini G, Gallenga G, Veltroni A. The treatment of burns with hyaluronic acid.|Translation of: Il trattamento delle ustioni con acido jaluronico.| *Hospitals of Italy Surgery/ Ospedali D'Italia Chirurgia* 1968; 19(3): 283–287.

Faulstich H. Weckauf M. Cytolysis of red cells mediated by phallolysin, a toxin binding to N –acetylglucosamine on the cell surface. *Hoppe–Seyler's Z. Physiol. Chem.* 1975; Bd. 356 (Jul.): 1187–1189.

Feige JJ, Pirollet F, Cochet C, Chambaz EM. Selective inhibition of a cyclic nucleotide–independent protein kinase (G–type casein kinase) by naturally occurring glycosaminoglycans. *FEBS Letters/Elsevier/ND Biomedical Press* 1980; 21(1): 139–142.

Forrester JV, Lackie JM. Effect of Hyaluronic acid on neutrophil adhesion. *J Cell Sci.* 1981; 50: 329–344.

Fraser JRE, Murcoch WS, Curtain CC, Watt BJ. Proteins retained with hyaluronic acid during ultrafiltration of synovial fluid. *Connective Tissue Research* 1977; 5: 61–65.

Gandrille S, Aiach M, Lane DA, Vidaud D, et al. Important role of Arginine 129 in Heparin–binding site of Antithrombin III. *J Biological Chemistry* 1990; 265(31): 18997–19001.

Gasior–Chrzan B, Gosciniak G, et al. Influence of white–egg lysozyme on *IStaphlyococcus aureus* phagocytosis by guinea–pig granulocytes. *Medycyna Doswiadczalan i Mikrobiologia* 1987; 39(7): 7–10.

Gaughan EM, Nixon AJ, Krook LP, Yeager AE, et al. Effects of sodium hyaluronate on tendon healing and adhesion formation in horses. *Am. J. Vet. Res.* 1991; 52(5): 764–773.

Gieldanowski Jerzy; Skowronska, Jadwiga. Studies on immunosuppressive and anti–inflammatory effect of adriamycin. *Arch. Immunol. Ther. Exp.* 1980; 28(3): 439–446.

Gill WB, Jones KW, Ruggiero KJ. Protective effects of heparin and other sulfated glycosaminoglycans on crystal adhesion to injured urothelium. *J Urology* 1982; 127(1): 152–154.

Gingerich DA. Effect of exogenous hyaluroxperimentally induced equine osteoarthritis: Dosage titration studies. *Research in Veterinary Science* 1981; 30: 192–197.

Ginsburg I. The biochemistry of bacteriolysis: Paradoxes, facts and myths. *Microbiological Sciences* 1988; 5(5): 137–142.

Ginsburg I, Sela MN, Morag A, Ravid Z, Duchan Z, et al. Role of leukocyte factors and cationic polyelectrolytes in phagocytosis of group A streptococci and *Candida albicans* by neutrophils, macrophages, fibroblasts and epithelial cells: Modulation by anionic polyelectrolytes in relation to pathogenesis of chronic inflammation. *Inflammation* 1981; 5(4): 289–312.

Goetinck PF, Stirpe NS, Tsonis PA, Carlone D. The tandemly repeated sequences of cartilage link protein contain the sites for interaction with hyaluronic acid. *J Cell Biology* 1987; 105: 2403–2408.

Gorog P, Raake W. Antithrombotic effect of a mucopolysaccharide polysulfate after systemic, topical and percutaneous application. *Arzneim.-Frosch.* 1987; 37(3): 342–345.

Granger HJ, Laine SH, Laine GA. Osmotic pressure exerted by entangled polysaccharide chains. *Microcirculation, Endothelium, and Lymphatics* 1985; 2: 85–105.

Graue EL, Polack FM, Balazs EA. The protective effect of Na–hyaluronate to corneal endothelium. *Exp. Eye Research*1980; 31: 119–127.

Gregoriadis G. Carrier potential of liposomes in biology and medicine (Part 1 of 2). *New England J Medicine* 1976; 295: 704–710.

Greiling H, et al. B–Elimination reaction in amino acid containing hyaluronic acid preparations. In: *Chemistry and Molecular Biology of the intercellular Matrix.* Edited by EA Balazs. New York: Academic Press, 1970: 759–762.

Gustafson SB, McIlwraith W, Jones RL. Comparison of the effect of polysulfated glycosaminoglycan, corticosteroids, and sodium hyaluronate in the potentiation of a subinfective dose of *Staphlyococcus aureus* in the midcarpal joint of horses. *Am. J. Vet. Res.* 1989; 50(12): 2014–2017.

Hakansson L, Vange P. The combined action of hyaluronic acid and fibronectin stimulates neutrohil migration. *Journal of Immunology* 1985; 135(4): 2735–2739.

Hakansson L, Hallgren R, Venge P. Regulation of granulocyte function by hyaluronic acid. *J. Clin. Invest.* 1980; 66: 298–305.

Hakansson L. Hyaluronic acid stimultes neutrophil function in vitro and in vivo. *Scandanavian J. Infectious Dis. Suppl.* 1980; 24: 54–57.

Hassan HG, Akerman B, Ranck H, Lindberg B, Lindquist B. Effects of adjuvants to local anaesthetics on their duration. *Acta Anaesthesiol. Scand.* 1985; 29: 384–388.

Hoshino O, Zehavi U, et al. The isolation and structure identification of a disaccharide containing manno–muramic acid from *Micrococcus lysodeikticus* cell wall. *Journal of Biological Chemistry* 1972; 247(2): 381–390.

Hughes EN, Colombatti A, Qugust JT. Murine cell surface glycoproteins. *J Biological Chemistry* 1983; 258(2): 1014–1021.

Hurd ER. Immunosuppressive and antiinflammatory properties of cyclophosphamide, azathioprine and methotrexate. *Arthritis and Rheumatism* 1973 (Jan.–Feb.); 16(1): 84–88.

Idson B. Polymers in skin cosmetics. *Cosmetics & Toiletries* 1988; 103: 63–68.

Idson B. Formulation for treatment of aging skin problems. *Drug and Cosmetic Industry* 1988; 142(Jan.): 36, 38, 84.

Idson B. "Natural" moisturizers for cosmetics. *Drug and Cosmetic Industry* 1985; 136(5)(May): 24–26.

Introini C, Mignini E. Lozione idratante dopo–bagno. *Rivista Italiana* 1973; 55(12): 804–811.

Iozzo RV. Proteoglycans: Structure, function, and role in neoplasia. *Laboratory Investigation* 1985; 53(4): 373–396.

Irwin DHG. Sodium hyaluronate in equine traumatic arthritis. *J. of the South African Veterinary Association* 1980; 50(4): 231–233.

Jacobs RR, McClain O, Neff J. Control of postlaminectomy scar formation: An experimental and clinical study. *Spine* 1980; 5(3): 223–229.

Jacobson B. The biosynthesis of hyaluronic acid. In: *Chemistry and Molecular Biology of the Intercellular Matrix:: vol. 2, Glycosamionglycans and Proteoglycans*, Edited by EA Balazs. New York: Academic Press, 1970.

Jarvelainen H, Ronnemaa T, Tammi M, et al. Type IIA hyperlipoproteinemic sera secrease the synthesis of hyaluronic acid by cultured human aortic smooth muscle cells. *Atherosclerosis* 1981; 39: 61–69.

Jeanloz RW. Mucopolysaccharides of higher animals. In: *The Chemistry and Biology of Compounds Containing Amino Sugars.* New York: Academic Press, 1969, pp. 589–625.

Johansson A, Hassan H, Renck H. Effects of adjuvants to local anaesthetics on their duration. *Acta Anaesthesiol. Scand.* 1985; 29: 736–738.

Joshi HN. In vitro characterization of membranes of hyaluronic acid and its esters. *Dissertation Abstracts International* 1993; 53(11): 5731–B.

Kalbhen DA. The inhibitory effects of steroidal and non--steroidal antirheumatic drugs on articular cartilage in osteoarthrosis and its counteraction by a biological GAG--peptide complex ("Rumalon"). *Zeitschrift fur Rheumatologie* 1982; 41(5): 340-202-211.

Katona G. A clinical trial of glycosaminoglycan–peptide complex ("Rumalon") in patients with osteoarthritis of the knee. *Current Medical Research and Opinion* 1987; 10(9): 625–633.

Katsu M, Abe T, Shimada S. Significance and clinical use of non–steroid anti–inflammatory drugs as substitutes for steroids in steroid dependence. *Nippon Rinsho* (1968 Jan.); 26(1): 89–95.

Keller N. Alteration of the hydrodynamic properties of hyaluronate solutions by corticosterone. *Biochimica et Biophysica Acta* 1967; 148: 757–766.

Kendall FE, et al. A serologically inactive polysaccharide elaborated by mucoid strains of group A hemolytic Streptococcus. *J Biological Chemistry* 1937; 118: 61–69.

Kielty CM, Whittaker SP, Grant ME, Shuttleworth CA. Typ VI collagen microfibrils: Evidence for a structural association with hyaluronan. *The Journal of Cell Biology* 1992; 118(4): 979–990.

Kimata K, Hascall VC, Kimura JH. Mechanisms for dissociating proteoglycan aggregates. *J Biol. Chemistry* 1982; 257(7): 3827–3832.

Kimoto E, Tanaka Y, Abe T. Interaction between acid mucopolysaccharides and basic noxious substances.*The Kurume Medical Journal* 1960; 7(1): 1–12.

Kirchberger MA, Martin DG, Leaf A, Sharp GW. The effect of aldosterone on glucose metabolism in toad bladder. *Biochimica et Biophysica Acta* 1968; 165: 22–31.

Kjems E, Lebech K. Isolation of hyaluronic acid from cultures of streptococci in a chemically defined medium. *Acta Path. Microbiol.. Scand.* 1976 (Sect. B); 84: 162–164.

Kopp S, Benneberg B, Haraldson T, Carlsson GE. The short–term effect of intra–articular injections of sodium hyaluronate and corticosteroid on temporomandibular joint pain and dynsfunction. *Oral Maxillofac. Surg.* 1985: 43: 429–435.

Kopp S, Carlsson GE, Haraldson T, Wenneberg. Long–term effect of intra–articular injections of sodium hyaluronate and corticosteroid on temporamandibular joint arthritis. *Oral. Maxillofac. Surg.* 1987; 45: 929–935.

Kreis H, Chkoff N, Droz D, et al. Nonsteroid antiinflammatory agents as a substitute treatment for steroids in ATGAM–treated cadaver kidney recipients. *Transplantation* 1984 (Feb.); 37 (2): 139–145.

Kresse von H, Truppe W. Untersuchungen zur pinozytose von proteoglykanen und glykosaminoglykanen. 1978; 17 Marz: 188–191.

Krusius T, Gehlsen KR, Ruoslahti E. A fibroblast chondroitin sulfate proteoglycan core protein contains lectin–like and grwoth factor–like sequences. *J Biol. Chemistry* 1987; 262(27): 13120–13125.

Ksander GA, Vistnes LM. Collagen and glycosaminoglycans in capsules around silicone implants. *J. Surgical Research* 1981; 31: 433–439.

Kvist TN, Finnegan CV. The distribution of glycosamionglycans in the axial region of the developing chick embryo II. Biochemical analysis. *J Exp. Zool.* vol. 175: 241–258.

Larsen NE, Balazs EA. Drug delivery systems using hyaluronan and its derivatives. *Advanced Drug Delivery Reviews* 1991; 7: 279–293.

Laurent TC. Structure of hyaluronic acid. In: *Chemistry and Molecular Biology of the Intercellular Matrix. Vols. i, II, III.* Edited by EA Balazs. New York: Academic Press, 1970, pp. 703–773.

Laurent TC. The interaction between polysaccharides and other macromolecules. *Biochemical Journal* 1963; 89(2): 253–257.

Laurent TC, Pietruszkiewicz A. The effect of hyaluronic acid on the sedimentation rate of other substances. *Biochimica et Biophysica Acta* 1961; 49(2): 258–264.

Laurent UBG, Granath KA. The molecular weight of hyaluronate in the aqueous humour and vitreous body of rabbit and cattle eyes. *Experemental Eye Research* 1983; 36: 481–492.

Laurent UBG, Fraser JRE. Turnover of hyaluronate in the aqueous humour and vitreous body of the rabbit. *Experimental Eye Research* 1983; 36:493–504.

LeBoeuf RD, Gregg RR, et al. Effects of hyaluronic acid and other glycosaminoglycans on fibrin polymer formation. *Biochemistry* 1987; 26: 6052–6057.

Lee KH, Spencer MR. Studies on mechanism of action of salicylates V: Effect of salicylic acid on enzymes involved in mucopolysaccharides synthesis. *J. Pharmaceutical Sciences* 1969; 58: 464–468.

LeVeen HH, Franklin E, Barberio JR. The use of hyaluronic acid for fixation of skin grafts. *Surgery* 1951; 29(5): 743–747.

Lindahl U, Hook M. Glycosaminoglycans and their binding to biological macromolecules. *Annual Review of Biochemistry* 1978; 47: 385–417.

Little CB, Hilbert BJ, Wickstrom S, Hedlund BE. Quantitative microanalysis of equine synovial fluid glycosaminoglycan concentration. *Am. J. Vet. Res.* 1990; 51(10): 1534–1539.

Longas OM, et al. Sequential hydrolysis of hyaluronate by B–Glucuronidase and B–N–Acetylhexosaminadase. *Biol. Chem. J.* 1981; 197: 275–282.

Lowther DA. The Role of glutamine in the biosynthesis of hyaluronate by streptococcal suspensions. *Biochemical Journal* 1956: 62: 304–314.

Maguen E, Besburn AB, Macy JI. Combined use of sodium hyaluronate and tissue adhesive in penetrating deratoplasty of corneal perforations. *Ophthalmic Surgery* 1984 (Jan.); 15: 55–57.

Malark JA, Nixon AJ, Skinner KL, Mohammed H. Characteristics of digital flexor tendon sheath fluid from clinically normal horses. *Am. J. Vet. Res.* 1991; 52(8): 12921294.

Mapleson JL, Buchwald M. Effect of cycloheximide and dexamethasone phosphate on hyaluronic acid synthesis and secretion in cultured human skin fibroblasts. *J. Cellular Physiology* 1981; 109: 215–222.

Markovitz A, et al. The biosynthesis of hyaluronic acid by group A Streptococcus. *J. Biological Chemistry* 1959; 234(9): 2343–2350.

Marmo E. Sulla farmacologia dei mucopolisaccaridi d'interesse reumatologico. *Cl. Terap.* 1979; 90: 531–539.

Maroudas NG, Lindenbaum ES. Polymer treatments reduce adhesion of comminuted stone in rat bladder. *British J Urology* 1987; 59: 519–522.

Martin DE, Reece M, Reese AC. Effect of plasma fibronectin, macrophages, and glycosaminoglycans on tumor cell growth. *Cancer Investigation* 1984; 2(5): 339–345.

Mazzone A, Baiguera R, Rossini S, et al. Pharmacological effect of yaluronic acid (HA) on phagocytes: Hypothesis for an HA–induced monocyte chemotatic factor for neutrophils. *Clinical Therapeutics* 1986; 8(5): 527–536.

Mazzone A, Baiguera R, Casali G, Tarantola M, et al. Importanza dell'acido ialuronico nel modulare la migrazione dei neutrofili. *Min. Med.* 1986; 77: 693–700.

McClean D. The capsulation of Streptococci and its relation to diffusion factor (hyaluronidase). *J Pathology & Bacteriology* 1941; 53: 13–27.

McCulloch JA. Chemonucleolysis: Experience with 2000 cases. *Clinical Orthopaedics and Related Research* 1980; 146 (Jan.–Feb.): 128–135.

McIlwraith W. Current concepts in equine degenerative joint disease. *Journal of the American Veterinary Medical Association* 1982; Feb. 1: 239–250.

Mehta PP, Sagar S, Kakkar VV. Treatment of superficial thrombophlebitis: A randomized, double–blind trial of heparinoid cream. *British Medical Journal* 1975; 3: 614–616.

Mejersjo C. TMJ Osteroarthrosis. *J Craniomandibular Practice* 1987; 5(1): 73–78.

Mejersjo C, Kipp S. Effect of corticosteroid and sodium hyaluronate on induced joint lesions in the guinea–pig knee. *Int. J. Oral Maxillofac. Surg.* 1987; 16: 194–201.

Mejersjo C. Ph.D. Thesis: Long–Term Development After Treatment of Mandibular Dysfunction and Osteroarthrosis: A Clinical–Radiographic Follow–Up and an Animal Experimental Study. Department of Stomatognathic Physiology, Faculty of Odontology, University of Goteborg, Goteborg, Sweden, 1984 (ISSN 0348–6672; ISBN 91-7222-758-3).

Mendler N, Schrock N. Osmotic properties of macromolecular solutions and gels: Physical Aspects and Physiological Relevance. In: *Hemodilution.: Theoretical Basis and Clinical Application.* Int. Symp. Rottach–Egern. Basel: Karger, 1972: 105–117.

Meyer K. Reflections on "mucopolysacharides" and their protein complexes. In: *Chemisry and Molecular Biology of the Intercellular Matrix vol. I.* Edited by EA Balazs. New York: Academic Press, 1970: pp. 5–24.

Meyer K, et al. The hydrolysis of the polysaccharide acids of vitreous humor, of umbilical cord, and of streptococcus by the autolytic enzyme of pneumococcus. *J. Biological Chemistry* 1937; 118: 71–78.

Miller D, Stegmann R. Use of Na–hyaluronate in auto–corneal transplantation in rabbits. *Ophthalmic Surgery* 1980; 11(1): 19–21.

Miyake K, Underhill CB, Lesley J, Kincade PW. Hyaluronate can function as a cell adhesion molecule and CD44 participates in hyaluronate recognition. *J Exp. Med.* 1990; 172: 69–75.

Miyazaki K, Goto S, Okawara H, Yamaguchi T. Sodium hyaluronate (SPH). *Pharmacometrics* 1984; 28(6): 1123–1135.

Mizushima Y. Possibility of non–steroid anti–inflammatory drugs as a substitute for steroids –analysis of the present situation and demands for the future. *Nippon Rinsho* (1968 Jan.); 26(1): 61–65.

Myers SL. Suppression of hyaluronic acid synthesis in synovial organ cultures by corticosteroid suspensions. *Arthritis and Rheumatism* 1985; 28(11): 1275–1282.

Nambisan B, Kurup PA. Ascorbic acid and glycosaminoglycan and lipid metabolism in guinea pigs fed normal and atherogenic diets. *Atherosclerosis* 1975; 22: 447–461.

Namiki O, Toyoshima H, Morisaki N. Therapeutic effect of intra–articular injection of high molecular weight hyaluronic acid on osteoarthritis of the knee. *International J Clinical Pharmacology, Therapy and Toxicology* 1982; 20(11): 501–507.

Neame PJ, Christner JE, Baker JR. Cartilage proteoglycan aggregates. *J Biol. Chemistry* 1987; 262(36): 17768–17778.

Neame PJ, Christner JE, Baker JR. The primary structure of link protein from rat chondrasarcoma proteoglycan aggregate. *J Biol. Chemistry* 1986; 261(8): 3519–3535.

Neame PJ, Perin J–P, Bonnet F, Christner JE, Jolles P, Baker JR. An amino acid sequence common to both cartilage proteoglycan and link protein. *J Biol. Chemistry* 1985; 260(23): 12402–12404.

Nehme D, Fingerhut B, Veenema RJ. Effect of a mucoopolysaccharide cream on tissue metabolism. *International Surgery* 1973; 58(3): 171–173.

Nettelbladt O, Tengblad A, Hallgren R. High–dose corticosteroids during bleomycin–induced alveolitis in the rat do not suppress the accumulation of hyaluronan (hyaluronic acid) in lung tissue. *Eur. Respir. J.* 1980; 3: 421–428.

Neubauer. Healon als Nothrelfer. *Klin. Mbl. Augenheilk.* 1983; 182: 269–271.

Niemann H, Birch–Andersen A, Kjems E, Mansa B, Stirm S. Streptococcal bacteriophage 12/12–borne hyaluronidase and its characterizarization as a lyase (EC 4.2.99.1) by means of streptococcal hyaluronic acid and purified bacteriophage suspensions. *Acta Path. Microbiol. Scand.* 1976 (Sect. B); 84: 145–153.

Nitzan DW, Pruzanski W, Saito S, Ranadive N. Modulation of locomotor activity of polymorphonuclear cells by cationic substances and cationic lysosomal fractions from human neutrophils. *Inflammation* 1985; 9(4): 375–387.

Nizolek DJH, White KK. Corticosteroid and hyaluronic acid treatments in equine degenerative joint disease: A review. *The Cornell Veterinarian* 1981; 71(4): 355–375.

O'Brien WF, Drake RS, Bibro MC. The use of ibuprofen and dexamethasone in the prevention of postoperative adhesion formation. *Obstetrics & Gynecology* 1982; 60(3): 373–378.

Ogielska E. Proby zastosowania etamucyny w odwarstwieniu siatkowki. *Klinika Oczna* 1973; 6: 671–672.

Ogston AG. The biological functions of the glycosaminoglycans. In: *Chemistry and Molecular Biology of the Intercelular Matrix. Vol. III.* Edited by EA Balazs. New York: Academic Press, 1970, pp. 231–1240.

Olesen ES. Fibrinolytic activity produced in guinea–pig serum by some human body fluids and by hyaluronic acid. *Scandinavian Journal of clinical & Laboratory Investigation* 1961; 13(1): 37–43.

Otsuka K, Mori Y. Inhibitory effect of D–penicillamine on degrqadation of hexosamine–containing substances in the involution of carrageenin granuloma induced by calcium chelate ethylenediaminetetraacetate. *Chem. Pharm. Bull.* 1976; 24(2): 215–219.

Pal MK, Nath J. Separation of hyaluronate, chondroitin sulfate, and heparin by adsorption–desorption technique. *Analytical Biochemistry* 1974; 57: 395–402.

Pantlitschko M, Schmid J, Seelich F, Kaiser E. Uber die blutgerinnungshemmende Eigenschaft sulfurierter hyaluronsaure. *Monatshefte Fur Chemie* 1951; 82: 380–383.

Passarini B, Tosti A, Fanti PA, Varotti C. Effetto dell'acido ialuronico sul processo reparativo delle ulcere trofiche. [Summary in English] *Giornale Italiano di Dermatologia e Venereologia* 1982; 117: XXVII–XXX.

Pigman W. Acide hyaluronique et facteurs de permeabilite tissulaire. *Bulletin de la Societe de Chimie Biologique* 1963; 45: 185–202.

Pigman W, et al. Preparation and stability of hyaluronic acid. *Biochim. Biophys. Acta* 1961; 53: 254–262.

Pinkus H, Perry ET. The influence of hyaluronic acid and other substances on tensile strength of healing wounds. *J. Investigative Dermatology* 1953; 21: 365–374.

Polefka TG. The passive permeability properties and cell surface characteristics of the novikoff hepatoma ascites cell. *Dissertation Abstracts International* 1980; 41(4): 1216B.

Popovici GG, Haulica I, Botez E. The action of some antibiotics on tissular diffusibility. *Revue Roumaine de Physiologie* 1971; 8(6): 503–509.

Pruett RC, Schepens CL, Constable IJ, Swann DA. Hyaluronic acid vitreous substitute. In: *Vetreous Surgery and Advances in Fundus Diagnosis and Treatment.* Freeman H.M., et al., Editors. Appleton–Century–Crofts, 1977: Chapter 55, pp. 433–444.

Pruzanski W, Ranadive NS, Saito s. Modulation of phagocytosis and intracellular bactericidal activity of polymorphonuclear and mononuclear cells by cationic proteins from human granulocytes. *Inflammation* 1984; 8(4): 445–457.

Raake W, Panse P, Elling H. Zur pharmakologie, pharmakokinetik und toxikologie eines Heparin–Analogs bei kutaner anwendung. *Die Medizinische Welt* 1986; 37: 67–71.

Razemon MM, Turut P, Capier M.J. L'acide hyaluronique dans les traumatismes delabrants du globes. *Bulletin des Societes d'Ophtalmologie du Nord. 1972: Seance du 29 Octobre.*

Reggianini V. L;azione locale dell'ac. jaluronico sui processi riparati viconnettivali. Risultati clinici. *Ospedali D'Italia Chirurgia* 1968; 19(2): 173–188.

Reim M, Teping C. Surgical procedures in the treatment of most severe eye burns. *Acta Ophthalmologica* 1989–Supplementum 192; 67: 47–54.

Repaske R, Repaske AC, Mayer RD. Carbon dioxide control of lag period and growth of *Streptococcus sanguis*. *J. Bacteriology* 1974; 117(2): 652–659.

Rosner IA, Boja BA, Malemud CJ, et al. Intraarticular hyaluronic acid injection and synovial prostaglandins in experimental immune synovitis. *J. Rheumatology* 1983; 10: 71–78.

Rydell NW, Balazs EA. Effect of intra–articular injection of hyaluronic acid on the clinical symptoms of osteoarthritis and on granulation tissue formation. *Clinical Orthopaedics and Related Research* 1971; 80(Oct.): 25–29.

Rydell NW, Butler J, Balazs EA. Hyaluronic acid in synovial fluid. VI Effect of intra–articular injection of hyaluronic acid on the clinical symptoms of arthritis in track horses. *Acta Veterinaria Scandinavica* 1970; 11(2): 139–155.

Saar(n)i H, Jalkanen M, Hopsu–Havu VK. Effect of five anti–inflammatory steroids on collagen and glycoaminoglycan synthessis in vitro. *British Journal of Dermatology* 1980; 103: 167–173.

Saar(n)i H, Tulamo R–M, Konttinen YT, Sorsa T. Methylprednisolone acetate induced release of cartilage proteoglycans: Determination by high performance liquid chromatolgraphy. *Annals of the Rheumatic Diseases* 1992; 51(2): 214–219.

Saar(n)i H, Hopsu–Havu VK. The decrease of hyaluronate synthesis by antiinflammatory steroids in vitro. *British Journal of Dermatology* 1978; 98: 445–449.

Saar(n)i H, Konttinen YT, Tulamo R–M, Antti–Poika I, Honkanen V. Concentration and degree of polymerization of hyaluronate in equine synovial fluid. *Am. J. Vet. Res.* 1989; 50(12): 2060–2063.

Saba P, Galeone F, Salvadorini F, Guarguaglini M, Ombrato M. Investigation of the antihyperlipemic activity of an association of clofibrate and extractive mucopolysaccharide complex. *Current Therapeutic Research* 1978; 23(4): 455–463.

Saba HI. Hemophilia and allied conditions. *Current Therapy* 1978; 280–288.

Salter MKC. Optical Studies of Acridine orange–glycosaminoglycan complexes in aqueous solution. *Dissertation Abstracts International* 1977; 12(Part 1): 6159B–6160B.

Schaefer H, Zesch A. Die penetration von heparin in die menschliche haut. *Pharmazie* 1976; 31: 251–254.

Schecter B, Neumann A, Wilchek M, Arnon R. Soluble polymers as carriers of cis–platinum. *J. Controlled Release* 1989; 10: 75–87.

Schmut O, Hofmann H. Preparation of gels from hyualuronate solutions. *Graefe's Arch. Clin. Exp. Ophthalmol.* 1982; 218: 311–314.

Schmut O, Hofmann H. A method for the purification of bovine vitreous body hyaluronic acid. *Biochimica et Biophysica Acta* 1981; 673: 192–196.

Schmut O, Hofmann H. Studies on the generation of hydrogen peroxide during some non–enzyme reactions changing the hyaluronic acid molecule. *Biochimica et Biophysica Acta* 1975; 411: 231–235.

Sertoli P, Merello A, Parodi M. L'acido jaluronico, per uso topico, nella cura delle lcere trofocircolatorie degli arti inferiori. (Comunicazioni). *Giornale Italiano di Dermatologia* 1970; 45(8): 468–471.

Shanley DJ, Cossu G, Boettiger D, Holtzer H, Pacifici M. Transformation by Rous Sarcoma Virus induces similar patterns of glycosaminoglycan synthesis in chick embryo skin febroblasts and bertebral chondroblasts. *J. Biol. Chemistry* 1983; 258(2): 810–816.

Shannon BT, Love SH, Roh BH, Schroff RW. Quantitation of glycosaminoglycans of rabbit lung during delayed–type hypersensitivity reactions and granuloma formation. *Inflammation* 1981; 5(4): 323–334.

Shannon BT, Love SH, Myrvik QN. Participation of hyaluronic acid in the macrophage disappearance reaction. *Immunological Communications* 1980; 9(4): 357–370.

Shcherbakova EB. Metabolism and functions of phagocytes on combined use of immunosuppressors and biologically active substances. *Antibiotiki* 1984; 29(12): 907–913.

Shepherd MG, Sullivan PA. The control of morphogenesis in *Candida albicans*. *J Dent. Res.* 1984; 63(3): 435–440.

Shimada E, Matsumura G. Molecular weight of hyaluronic acid from rabbit skin. *J. Biochemistry* 1977; 81: 79–91.

Singh Ch, Misra J. Some properties of deoxycholate and dodecyl sulphate in relation to macroionic complexes and their biochemical implications. *Arzneim.-Forsch.* 1978; 28(8): 1320–1327.

Sneader WE, Florence At, McColl E. A possible mechanism for the action of dimethyl sulphoxide on percutaneous absorption. *J. Pharmacy & Pharmacology* 1971; 23 (Suppl.): 252s.

Sparer RV. Controlled Release of Drugs from Glycosaminoglycan Drug Complexes. *Dissertation Abstracts International* 1983; 43(9): 2921B.

Stacey M, Barker SA. Hyaluronic acid. In: *Carbohydrates of Living Tissues*. By: Stacey M, Barker SA. London: D. Van Nostrand Co. Ltd., 19 62: 37–58.

Stangel JJ, Nisbet II JD, Settles H. Formation and prevention of postoperative abdominal adhesions. *J Reproductive Medicine* 1984; 29(3): 43–156.

Stegman R, Miller D. Use of sodium hyaluronate in severe penetrating ocular trauma. *Acta Ophthalmol.* 1986; 18: 9–13.

Stegman R, Miller D. Extracapsular cataract extraction with hyaluronate sodium. *Annals of Opthalmology* 1982; Sep.: 813–815.

Stenfors L–E. Treatment of tympanic membrane perforations with hyaluronan in an open pilot study of unselected patients. *Acta Otolaryngol (Stockh)* 1987; Suppl. 442: 81–87.

Stephebs RW, Ghosh P, Taylor TKF. The inhibitory effects of anti–inflammatory drugs and cations on hyaluronic acid degradation by serum and pathological synovial fluid polysaccharidases. *Clinical and Experimental pharmacology and Physiology*. Abstract No. 91: 87–88.

Stoolmiller AC, Dorfman A. The biosynthesis of hyaluronic acid in group A Streptococci. In: *Chemistry and Molecular Biology of the Intercellular Matrix*. Edited by EA Balazs. Boston: Academic Press, 1970, pp. 783–794.

Stuttgen G, Panse P, Bauer E. Permeation of the human skin by heparin and mucopolysaccharide polysulfuric acid ester. *Arzneim.-Forsch.* 1990; 40(4): 484–489.

Sugahara et al. Biosynthesis of HA by Streptococcus. *J. Biological Chemistry* 1979; 254(14): 6252–6261.

Suzuki, Sakaru. (Dep't. of Chemistry, Faculty of Science, Nagoya University.) Symposium III Interaction between cell Stromata and Cancer: Interaction between Cells and Stromata in the Course of Cancer Cell Metastasis. [English Translation] *Japanese Journal of Cancer and Chemotherapy* 1984; 11(3): 557–780.

Swann DA, Radin EL, Nazimiec M, Weisse PA, Curran N, et al. Role of hyaluronic acid in joint lubrication. *Ann. Rheum. Dis.* 1974; 33: 318–326.

Swann DA. On the state of hyaluronic acid in a connective tissue matrix. In: *Chemistry and Molecular Biology of the intercellular Matrix*. Edited by EA Balazs. New York: Academic Press, 1970: 743–748.

Swann DA. Studies on hyaluronic acid: The preparation and properties of Rooster Comb hyaluronic acid. *Biochem. Biophys. Acta.* 1968; 156: 17–30.

The New Encyclopaedia Britannica, vol. VIII. 1977: p. 102.

Thomas SC, Jones LC, Hungerford DS. Hyaluronic acid and its effect on postoperative adhesions in the rabbit flexor tendon: A preliminary look. *Clinical Orthopaedics and Related Research* 1986; 206: 281–289.

Toledo–Pereyra LH, Simmons RL, Najarian JS. Modification of imunogenicity on kidney allografts treated with acid mucopolysaccharides. *Surgical Forum.* pp. 331–332.

Tonn SJ, Gander JE. Biosynthesis of polysaccharides by prokaryotes. *Ann. Rev. Microbiol.* 1979; 33: 169–199.

Torregrossa F, Caroti A. Una verifica clinica sull'isp tpocp do acodp oa; irpmocp spttp fpr,a do garze mpm adesove nella terapia di ulcere ad andamento torpido. *Giornale Italiano di Dermatoligia e Venereoligia* 1983; 118: XLI–X-LIV.

Trabucchi E, Foschi D, Marazzi M, Radaelli E, Lucianetti A, Rizzitelli E, Baratti C, et al. Prevention of wound dehiscence in severely obese patients with jejuno–ileal by–pass: The role of hyaluronic acid. *Pharmatherapeutica* 1988; 5(4): 233–239.

Treadway WJ, et al. The role of hyaluronic acid flux on modulation of neutrophil function. *Arthritis and Rheumatism* 1981; 24(4) (Suppl): 218.

Trimble WS, Johnson PW, Hozumi N, Roder JC. Inducible cellular transformation by a metallothionein –ras hybrid oncogene leads to natural killer cell susceptibility. *Nature* 1986; 321: 782–784.

Tulamo R–M. Comparison of high–performance liquid chromatography with a radiometric assay for determination of the effect of intra–articular administration of corticosteroid and saline solution on synovial fluid hyaluronate concentration in horses. *Am. J. Vet. Res.* 1991; 52(12): 1940–1944.

Tulamo R–M, Saar(n)i H, Konttinen YT. Determination of concentration of hyaluronate in equine serum. *Am. J. Vet. Res.* 1990; 51(5): 740–742.

Turley EA, Austen K, Vandeligt, Clary C. Hyaluronan and a cell–associated Hyaluronan binding protein regulate the locomotion of Ras–transformed cells. *The Journal of Cell Biology* 1991; 112(5): 1041–1047.

Turley E, Tretiak M, Tanguay K. Effect of glycosaminoglycans and enzymes on the integrity of human placental amnion as a barrier to cell invasion. *JNCI* 1987: 78; 787–795.

Underhill CB, Green SJ, Comoglio PM, Tarone G. The hyaluronate receptor is identical to a glycoprotein of Mr 85,000 (gp85) as shown by a monoclonal antibody that interferes with binding activity. *J Biol. Chem.* 1987; 262(27): 13142–13146.

Uzuka M, et al. The mechanism of estrogen–induced increase in hyaluronic acid biosynthesis, with special reference to estrogen receptor in the mouse–skin. *Biochimica et Biophysica Acta* 1980; 627: 199–206.

Vaheri A. Heparin and related polyionic substances as virus inhibitors. *Acta Pathologica et Microbiologica Scandinavica. Supplementum* 174, 1964: 1–98.

van de Rijn I, van de, Kessler RE. Growth characteristics of Group A Streptococci in a new chemically defined medium. *Infection and Immunity* 1980; 27(2): 444–448.

Venturini D. Osservazioni cliniche sull'impiego dell'acido ialuronico in terapia dermatologica. *Giornale Italiano di Dermatologia e Venereologia* 1985; 120: V–X.

Verstraeten TC, Wilcox DK, Friberg TR, Reel C. Effects of silicone oil and hyaluronic acid on cultured human retinal pigment epithelium. *Investigative Ophthalmology & Visual Science* 1990; 31(9): 1761–1766.

Vuorio E, Takala I, et al. Effects of sodium aurothiomalate on hyaluronic acid synthesis in normal and rheumatoid synovial fibroblast cultures. *Scandinavian Journal of Rheumatology* 1979; 8: 173–176.

Walther M. The prevention of striae cutis distansae during pregnancy. [*Il trattamento preventivo delle ante la gravidanza*] *Minerva Ginecologica* 1981; 33: 497–499.

Wasteson A, Westermark B, Lindahl U, Ponten J. Aggregation of feline lymphoma cells by hyaluronic acid. *Int. J Cancer* 1973; 12: 169–178.

Weirich EG, Longauer Jk, Kirkwood AH. Dermatopharmacology of salicylic acid. III. Topical contrainflammatory effect of salicylic acid and other drugs in animal experiments. *Dermatologica* 1976; 152(2): 87–99.

Welter DA, Hodge LD. A scanning electron microscopic technique for three-dimensional visualization of the spatial arrangement of metaphase, anaphase and telophase chromatids. *Scanning Electron Microscopy* 1985; II: 879–888.

Whitnack E, Bisno AL, Beachey EH. Hyaluronate capsule prevents attachment of group A streptococci to mouse peritoneal macrophages. *Infection and Immunity* 1981; 31(3): 985–991.

Wigrin A, Falk J, Wik O. The healing of cartilage injuries under the influence of joint immobilization and repeated hyaluronic acid injections. *Acta Orthop. Scand.* 1978; 49: 121–133.

Willen J. Diagnostik och behandling av istabila frakturer i brost–och landryggrad. *Nordisk Medicin* 1985; 100: 8–10.

Wolf RE, et al. Growth–rate–dependent alteration of 6–phosphogluconate dehydrogenase and glucose 6–phosphate dehydrogenase levels in *Escherichia coli* K–12. *J. Bacteriology* 1979; 139(3): 1093–1096.

Wu TC, Trask LM, Phee RE. Comparison of media and culture techniques for detection of *Streptococcus pneumoniae* in respiratory secretions. *J Clinical Microbiology* 1980; 12(6): 772–775.

Yaron M, Yaron I, Herzberg M. Levamisole in rheumatoid arthritis [letter]. *Lancet* 1976; Feb. 14: 369.

Yuzawa K. Experimental studies on the healing and restoration of gliding function of the injured digital flexor tendon. [Summary in English] *J. Jpn. Orthop. Ass.* 1985; 59: 1107–1118.

Zakut–Houri R, Oren M, Bienz B, Lavie V, Hazum S, Givol D. A single gene and a pseudogene for the cellular tumour antigen p53. *Nature* 1983; 306: 594–497.

TREATMENT OF DISEASE AND CONDITIONS ASSOCIATED WITH MACROPHAGE INFILTRATION

This application is a continuation in part of application Ser. No. 08/200,309 filed Feb. 23, 1994 non U.S. Pat. No. 5,679,857, which is a continuation of application Ser. No. 07/838,673 filed Feb. 21, 1992 now abandoned, the contents of which are each incorporated herein by reference. This application is also a Continuation-In-Part of application Ser. No. 07/675,908 filed Jul. 3, 1991, whose contents is incorporated herein by reference.

FIELD OF INVENTION

This invention relates to the treatment of diseases and conditions characterized by leukocyte [e.g. white blood cells] infiltration into the area damaged by the disease or condition for example in oxygen and/or glucose deprived tissue in the human body. This invention finds one application in the treatment of stroke. This invention finds another application in the treatment of infarcts (myocardial infarction). This invention also finds application in the treatment of any disease or condition characterized by leukocyte [e.g. white blood cells] infiltration to the area of damaged tissue of the body.

BACKGROUND OF THE INVENTION

When tissue (and the individual cells) are deprived of oxygen and/or glucose, the cells and consequently the tissue made up by the cells are damaged. As a result, among other responses, an inflammatory response (reaction) is set up in the area (site) of the damage. This inflammatory response includes, among other responses, the migration of inflammatory cells (for example macrophages, neutrophils, and other white blood cells) to the site of the damage.

For example, during a stroke or infarct (e.g. myocardial infarction, heart attack), whatever the cause, the blood supply in the blood vessels is impaired and diminished. The consequences include deprivation of oxygen and glucose resulting in, at the very least, damage to the deprived areas.

This damage sets, among other responses, an inflammatory response in the area damaged with the consequent migration of inflammatory cells (macrophages, neutrophils and other white blood cells). Because of the damage (trauma) to the site, prostaglandin synthesis also increases.

Cerebral deprivation of oxygen and glucose in premature birth follows the same scenario—a deprivation of oxygen to the brain of the infant which sets up an inflammatory response (migration of inflammatory cells (for example macrophages, neutrophiles and other white blood cells).

It is therefore an object of this invention to provide pharmaceutical compositions (for example, injectibles (sterile)), methods of treatment, and new uses for known chemicals which reduce the damage caused to the tissue and cells (when the compositions are employed), for example, resulting from a stroke, infract (myocardial infarction) and/ or any disease or condition characterized by an inflammatory response for example by macrophage, neutrophil or other white blood cell infiltration or migration into the area of the damage.

It is a further object of this invention to provide pharmaceutical compositions, methods of treatment and new uses of known chemicals which downregulate the cells' activity (macrophages, neutrophils and other white cells) and thus modify (alter) the body's anti-inflammatory response.

Further and other objects of the invention will be realized by those skilled in the art from the following summary of invention and detailed description of embodiments thereof.

SUMMARY OF THE INVENTION

According to one aspect of the invention, when tissue and thus cells are damaged for example by being deprived of glucose and/or oxygen, the activity of inflammatory cells (for example macrophages, neutrophils and other white blood cells) will be modulated (for example their migration into the area (to the site) of damage will be diminished), by the administration of an effective amount of hyaluronic acid and/or salts thereof (for example sodium hyaluronate) at the time the area is being damaged (as for example at the time of a stroke or infarct or other disease or condition which is characterized by macrophage, neutrophile or other white blood cell infiltration into the area of the tissue damaged by the condition and/or disease or a short time thereafter. While Applicant should not be limited to the following mechanism of action of the invention, Applicant believes that the administration of the hyaluronic acid and/or salts thereof (e.g. sodium salt) blocks, for example by binding with, the hyaluronic acid (HA) receptors of the inflammatory cells (for example macrophages, neutrophiles and other white blood cells), thus blocking their migration into the area of the damaged tissue.

The preferred form of hyaluronic acid is sodium hyaluronate having a molecular weight less than 750,000 daltons for example 10,000–300,000 daltons.

To supplement this inhibition (blockage) of the inflammatory response, (which inflammatory response causes the migration or infiltration of the macrophages, neutrophiles or other white blood cells into the damaged area), NSAIDS may also be given with the form of hyaluronic acid which blocks (for example binds with) the HA receptors. Thus inhibition of prostaglandin synthesis can be achieved.

The hyaluronic acid and/or salts (preferably sodium hyaluronate having a molecular weight less than 750,000 daltons) may be utilized at varying doses (depending upon the method of administration) from 1–10 mg/kg body weight to 15–20 mg/kg of body weight or more, for example a dose in excess of 25 mg/kg and more to over 3000 mg/70 kg person. In adult human (and adult rats) excess amounts of the form of hyaluronic acid are tolerated, however in rat neonates, excess can and does cause damage.

Thus and according to another aspect of the invention when an NSAID for example indomethacin (dissolved in n-methyl glucamine (nmg)) or other NSAID is administered with greater than 200 mg hyaluronic acid per 70 kg person with 1–2 mg/kg body weight of the NSAID (in one instance indomethacin and NMG), no major toxic side effects occur such as gastro-intestinal distress, neurological abnormalities, depression, etc., even at elevated amounts of indomethacin (if necessary). If the amount of hyaluronic acid is decreased below that amount, the usual side effects of using an NSAID may begin to reoccur. The same can be said with other therapeutic agents, no major toxic side effects occur with the administration of greater than 200 mg hyaluronic acid (e.g., sodium hyaluronate per 70 kg person.

Preferably (and on the basis of tests performed) each preferred dosage amount of the preferred form of hyaluronic acid, sodium hyaluronate, should be in the order of about 10–25 mg/kg body weight, for example in the order of about 1800 mg/70 kg person if administered subcutaneously for example in the back. Intravenous dosing could employ smaller (lesser) dose amounts of the form of hyaluronic acid. Preferred amounts are 10–20 mg./kg of body weight of a human.

Presently testing in neonate rats reveals that suitable dosage amounts will establish a concentration volume of the chosen form of hyaluronic acid (for example sodium hyaluronate) of about 3 mg/ml of blood in an adult human. When administered, an amount of between about 10 mg of, for example, sodium hyaluronate/kg and about 25 mg of, for example, sodium hyaluronate/kg of body weight of an adult human is administered. More recent tests with rats neonates, achieved levels of hyaluronic acid (12 hours after administration subcutaneously in the neonates) at 10 mg/kg in their blood. These amounts can be adjusted up or down as would be deemed preferable in the circumstances.

The administration preferably starts at the time of the disease or condition (for example stroke or mycardial infarction) occurring or shortly thereafter (within 24 hours) and continues until such time as not required. Preferably the level achieved is maintained in the blood. For example a level of 15 mg/kg of body weight is established in the blood, by initial intravenous administration. Then that level is maintained by for example subcutaneous administration (for example, by subcutaneous injection).

NSAIDS may be given at the same time in effective amounts (e.g. 1–2 mg/kg of body weight in the case of indomethacin.

Drugs for the treating of a mycardial infarction or stroke may also be administered such as a clot dissolving drug. Clot dissolving drugs comprise TPA, Streptokinase (proteolytic product), Urokinase and the like. Other available drugs are the NSAID acetylsalicylic acid (aspirin), beta blockers, heparin, a plasminogen activator, and other suitable drugs.

In addition to the NSAIDS, other drugs (where a stroke is or has occurred) may be administered with the form of hyaluronic acid (for example sodium hyaluronate having a molecular weight less than 750,000 daltons for example 300,000 daltons) with or without the NSAIDS. These drugs would be in their expected amounts. These drugs may be for example the same as above and may also comprise anti-platelet drugs for example those which alter the platelet function (prevent agreregation) and prevent thrombis formation (clots).

One form of hyaluronic acid and/or salts thereof (for example sodium salt) and homologues, analogues, derivatives, complexes, esters, fragments, and sub units of hyaluronic acid, preferably hyaluronic acid and salts and thereof suitable for use with Applicant's invention is a fraction supplied by Sterivet Laboratories Limited. One such fraction is a 15 ml vial of Sodium hyaluronate 20 mg/ml (300 mg/vial-Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) may comprise the following characteristics:

a purified, substantially pyrogen-free fraction of hyaluronic acid obtained from a natural source having at least one characteristic selected from the group consisting of the following:

(i) a molecular weight within the range of 150,000–225,000;

(ii) less than about 1.25% sulphated mucopolysaccharides on a total weight basis;

(iii) less than about 0.6% protein on a total weight basis;

(iv) less than about 150 ppm iron on a total weight basis;

(v) less than about 15 ppm lead on a total weight basis;

(vi) less than 0.0025% glucosamine;

(vii) less than 0.025% glucoronic acid;

(viii) less than 0.025% N-acetylglucosamine;

(ix) less than 0.0025% amino acids;

(x) a UV extinction coefficient at 257 nm of less than about 0.275;

(xi) a UV extinction coefficient at 280 nm of less than about 0.275;

(xii) a pH within the range of 7.3–7.9.

Preferably the hyaluronic acid is mixed with water and the fraction of hyaluronic acid fraction has a mean average molecular weight within the range of 150,000–225,000. More preferably the fraction of hyaluronic acid comprises at least one characteristic selected from the group consisting of the following characteristics:

(i) less than about 1% sulphated mucopolysaccharides on a total weight basis;

(ii) less than about 0.4% protein on a total weight basis;

(iii) less than about 100 ppm iron on a total weight basis;

(iv) less than about 10 ppm lead on a total weight basis;

(v) less than 0.00166% glucosamine;

(vi) less than 0.0166% glucuronic acid;

(vii) less than 0.0166% N-acetylglucosamine;

(viii) less than 0.00166% amino acids;

(ix) a UV extinction coefficient at 257 nm of less than about 0.23;

(x) a UV extinction coefficient at 280 nm of less than 0.19; and (xi) a pH within the rant of 7.5–7.7.

Other forms of hyaluronic acid and/or its salts, and homologues, derivatives, complexes, esters, fragments and sub units of hyaluronic acid may be chosen from other suppliers, for example those described in the prior art documents previously referred to. In addition Applicants have propose sodium hyaluronate produced and supplied by LifeCore™ Biomedical, Inc. having the following specifications

| Characteristics | Specification |
|---|---|
| Appearance | White to cream coloured particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |

| Heavy Metals, maximum ppm | | | | | | | | |
|---|---|---|---|---|---|---|---|---|
| As | Cd | Cr | Co | Cu | Fe | Pb | Hg | Ni |
| 2.0 | 5.0 | 5.0 | 10.0 | 10.0 | 25.0 | 10.0 | 10.0 | 5.0 |

| Microbial Bioburden | Non observed |
|---|---|
| Endotoxin | <0.07 EU/mg NaHy |
| Biological Safety Testing | Passes Rabbit Ocular Toxicity Test |

The administration may take place subcutaneously, intravenously or by injection.

DETAILED DESCRIPTION OF EMBODIMENTS

The invention will now be illustrated with respect to the following example.

EXPERIMENT 1

Seven day old Fischer rat neonates were injected subcutaneously with sodium hyaluronate (MW 300,000 daltons) in the back ½ hour before the operation with 0.6 mg of sodium hyaluronate /60ul/animal. Animals were then injected once a day for seven days after the operation and euthenized 14 days after the operation. The right carotid artery was ligated for 1 hour (induced stroke). The animals were then placed in incubators containing 8% oxygen. (The left side was not tied off and provided a suitable control.) Brain damage was readily produced in control animals by day 4 and 7 as determined by nissl staining (for nerves) and for gliosis including increased staining for GFAP, connexin 43, and macrophages (ED-1 epitope). As well increased staining for hyaluronan receptors was observed with CD44 increased in macrophages and astrocytes while RHAMM was increased in neuronal cells and subsets of macrophages. As well damage was observed morphologically where neuronal loss was evident and the right half of the brain had collapsed. Animals treated with HA for 7 days were euthanized at 14 days (as were controls run with these experiments) and none of the above parameters were positive. That is there is no evidence of brain collapse, neuronal loss, macrophage influx or increase in the expression of gliotic proteins or hyaluronan receptors. The hyaluronan treated animal's brains appeared morphologically normal, although functional test for neuronal activity have not yet been done. In the absence of any obvious morphological changes, extensive functional damage would not be expected.

The dose used for each animal was 0.6 mg of sodium hyaluronate (Molecular Weight 300,000 daltons) per 23 g animal by subcutaneous administration so for a human of 70 kg this would mean a 1.8 g subcutaneous dose/person. An intravenous dose would be smaller. There are approximately 85 cc blood/kg in humans. Therefore an average adult would have about 6000 cc (70 kg person). Thus the concentration achieved is in the order of 0.3 mg of sodium hyaluronate/1 ml or cc of blood. Administration to achieve this concentration is in the order of 25 mg/kg of body weight for humans.

EXPERIMENT 2

Experiment 2 repeated Experiment 1 only the right carotid artery was ligated for 3 hours (2 hours longer than the 1 hour specified in Experiment 1) to accrue more brain necrosis. In Experiment 2 the same amount of sodium hyaluronate (HA) (0.6 mg of sodium hyaluronate) was administered to each neonate (regardless of the actual weight of the neonates) and each animal received an injection of sodium hyaluronate subcutaneously at the time of the operation.

Twelve hours after subcutaneous administration, blood levels of 15–20 mg/kg of HA are obtained. Continued analysis of blood levels indicates that HA levels remain at 15 mg/kg for 24 hours.

After the operation, we continued to inject HA in the same dosage amounts every 24 hours for 7 days. At no time during the 7 days did the HA levels drop below 15 mg/kg.

The brains of the animals (including controls) were examined at 2 weeks.

Of the three animals injected with HA, the brains were in the same condition as the brains of the neonates administered with HA in Experiment 1. The one control suffered excessive brain damage. As a result of these tests, we have concluded that dose amounts of as low as 1 mg/kg of body weight of the animal will be therapeutic (e.g. for blocking the infiltration of macrophages, neutrophiles and other white blood cells into the area (to the site) of the stroke. Dose amounts of 10 mg or more of HA/kg of the animal (human) are preferred for example 10–20 mg/kg of body weight.

EXPERIMENT 3

While humans and adult rats are able to tolerate excesses of sodium hyaluronate (HA), rat neonates are not as tolerant. Thus, in Experiment 3, where the rate neonates were smaller, dosage amounts of 25 mg/kg of HA, administered in Experiment 3, resulted in damage to the brains of the neonates.

EXPERIMENT 4

Four rats were each exposed to isoproteranol to induce myocardial infarction (heart attack) in each. The administration of isoproteranol for inducing an infarct is a commonly known technique as would be understood by persons skilled in the act and is not elaborated herein. Each of two of the rats was immediately after the infarct injected with sodium hyaluronate (Molecular Weight 300,000 daltons) (HA) in the amount of 15 mg/kg. The subcutaneous injections continued for seven days (one subcutaneous injection each day). Twelve hours after the initial injection, the blood levels of HA were 10 mg/kgm body weight in the blood system of each rat.

The other two rats were immediately after the induction of the infarct each injected subcutaneously with saline (as a control). The subcutaneous injections continued for seven days, one injection per day. The rats were then sacrificed. In the saline-treated animals, heart tissue was necrotic with massive amounts of accumulated white cells. In the HA-treated rats, no damage was observed in the heart tissue and no white cells were apparent (as determined by E0-1 staining of frozen sections).

As a result, we have concluded that dosage amounts of 10–25 mg/kg of body weight administered to humans is appropriate. While lesser amounts can still be therapeutic, they will not give optimal results. Optimal results are the goal in the treatment of each of a stroke and myocardial infarction.

Preferably the chosen dosage amount of the HA is initially given intravenously to establish the desired levels of HA in the blood. Thereafter, these levels are maintained for example by administration subcutaneously (subcutaneous injection). Preferred blood levels appear to be starting in the order of 10 mg/kg.

As many changes can be made to the preferred embodiments of the invention without departing from the scope of the invention, it is intended that all material contained herein be interpreted as illustrative of the invention and not in a limiting sense.

The embodiments of the invention in which an exclusive property or privilege is claimed are as follows:

1. A method of treating a human having a disease or condition characterized by white blood cell infiltration into an area damaged by the disease or condition, the method comprising administering to the human an effective amount of a form of hyaluronic acid selected from the group consisting of hyaluronic acid and pharmaceutically acceptable salts thereof for a period of time until the administration is no longer required.

2. The method of claim 1 wherein the effective amount of the form of hyaluronic acid is in the order of between about 10 mg to about 25 mg per kilogram of body weight.

3. The method of claim 2 wherein the disease or condition is a stroke.

4. The method of claim 2 wherein the disease or condition is myocardial infarction.

5. The method of any of claims 1 or 2 wherein the treatment starts within about 24 hours of the detection of the disease or condition and continues until no longer required.

6. The method of any of claims 1, 2, 3 or 4 wherein the form of hyaluronic acid is sodium hyaluronate having a molecular weight less than 750,000 daltons.

7. The method of claim 1, 2, 3 or 4 wherein the form of hyaluronic acid is sodium hyaluronate and is administered by a route of administration selected from the group consisting of intravenous administration, subcutaneous injection and combinations thereof.

8. The method of claim 1 wherein the concentration of the hyaluronic acid in a human after administration is at least 0.3 mg/ml of blood.

9. The method of claims 1, 2, 3, 4, or 8 further comprising administration of an effective amount of a medicine selected from the group consisting of an NSAID, an anti-stroke drug, Beta blocker acetylsalicylic acid, streptokinase anti-platelet drugs, heparin and a plasminagen activator or combinations thereof.

10. The method of claims 1, 2, 3 or 4 wherein the blood levels of the form of hyaluronic acid achieved is greater than about 10 mg/kg of body weight of the person.

* * * * *